US007822622B2

(12) United States Patent
Kaindl et al.

(10) Patent No.: US 7,822,622 B2
(45) Date of Patent: Oct. 26, 2010

(54) SYSTEM AND METHOD FOR MEDICAL APPOINTMENT AND EXAMINATION SEQUENCE PLANNING

(75) Inventors: Herbert Kaindl, Wiener-Neustadt (AT); Heintje Wyczisk, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1447 days.

(21) Appl. No.: 10/956,265

(22) Filed: Oct. 1, 2004

(65) Prior Publication Data

US 2005/0075906 A1  Apr. 7, 2005

Related U.S. Application Data

(60) Provisional application No. 60/507,658, filed on Oct. 1, 2003.

(51) Int. Cl.
*G06Q 10/00* (2006.01)
*G06Q 50/00* (2006.01)
(52) U.S. Cl. .......................................................... 705/2
(58) Field of Classification Search .................. 705/2–3
See application file for complete search history.

(56) References Cited

U.S. PATENT DOCUMENTS 6,147,773 A * 11/2000 Taylor et al. ................. 358/400
6,345,260 B1 * 2/2002 Cummings et al. ............. 705/8
6,535,883 B1 * 3/2003 Lee et al. ..................... 707/100
7,065,586 B2 * 6/2006 Ruttenberg et al. ......... 709/244
7,337,123 B2 * 2/2008 Dvorak et al. .................. 705/8
7,379,885 B1 * 5/2008 Zakim ........................... 705/2
7,464,040 B2 * 12/2008 Joao .............................. 705/2
2002/0085026 A1  7/2002 Bocionek et al.
2003/0212580 A1 * 11/2003 Shen .............................. 705/2

FOREIGN PATENT DOCUMENTS

DE  101 54 740  6/2002

* cited by examiner

*Primary Examiner*—Gerald J. O'Connor
*Assistant Examiner*—Reginald Reyes
(74) *Attorney, Agent, or Firm*—Schiff Hardin LLP

(57) ABSTRACT

A method and appertaining system to implement the method optimizes a series of medical procedures/examinations to be performed on a patient by utilizing information and attributes including possibly medical facility attributes, medical department attributes, equipment attributes, personnel attributes, patient generic attributes, patient specific attributes, and medical procedure attributes. A catalog of rules is utilized by the scheduling system to ensure that times between procedures/examinations are optimized and do not violate any rules or constraints of the system. Additionally, portions of the method and system may be utilized to check an existing schedule and provide information to a user without actually modifying the schedule itself.

20 Claims, 19 Drawing Sheets

Interval Warning

| Examination 1 | Date | Examination 2 | Date | Selected Interval | Recommended Interval |
|---|---|---|---|---|---|
| CT:CTHAL | 2003.03.31 11:45 | MR:MRHAL | 2003.03.31 10:50 | 0:00:35 | 1:00:00 |

Ignore    Correct

| Examination / Procedure | Rule/Constraint |
|---|---|
| ultrasound | • before gastroscopy, or one day later<br>• either before an examination with barium contrast agent, or three days afterwards<br>• before an angiography, or 24 hours later<br>• no irrigation three days before and two days after an ultrasound |
| abdominal ultrasound | • before ERCP (Endoscopic Retrograde Cholangio Pancreatography), or one day later |
| abdominal puncture | • before irrigation, or three days later<br>• before gastroscopy, or three days later |
| drainage | • before irrigation, or three days later<br>• before gastroscopy, or three days later |
| MR | • either before a biopsy or seven days later<br>• no more than 1 MR on one day<br>• MR using contrast agent and CT using contrast agent are not to be performed on the same day |
| X-ray | • before an angiography, or 24 hours later |

FIG. 6A

| Examination / Procedure | Rule/Constraint |
|---|---|
| angiography | • before irrigation, or three days later<br>• before stomach x-ray, or three days later<br>• before enteroclysma, or three days later<br>• before examinations using contrast agent containing barium, or three days afterwards<br>• (except for MR angiography) and CT using contrast agent are not to be performed on the same day |
| first irrigation | • then stomach x-ray (if reversed, wait 2-3 days) |
| x-rays (abdominal, renal) | • before an examination using contrast agent or three days afterwards<br>• IVU (renal x-rays) and CT with contrast agent are not to be performed on the same day |
| bone x-rays of the spinal column or of the pelvis | • either before a contrast agent examination using oral contrast agent or 1-7 days afterwards (depending on age) |

FIG. 6B

| Examination / Procedure | Rule/Constraint |
|---|---|
| examinations using contrast agents containing barium | • stomach x-rays, irrigation=intestinal x-ray, enteroclysma<br>• if, after an abdominal CT (contrast agent containing barium), performance of an MR in the same area is desired, the contrast agent has a disturbing effect; for this reason it is necessary to wait one day, or two days if the patient is 70 years of age or older.<br>• First the x-rays (abdominal, renal, skeletal bones, pelvis, and lumbar) are made, then the contrast agent examination is carried out.<br>• either before a abdominal puncture or three days later<br>• No examination using contrast agent containing barium before an IVU; if this has already been carried out: wait three days |
| CT using contrast agent containing barium | • either before a stomach x-ray or seven days afterwards<br>• either before an intestinal x-ray or six days afterwards (depending on age) |
| bone density measurements of the lumbar region | • oral contrast agent is in no case to be used  B  after a week, normal results are again obtained |
| endosonography | • before CT with oral contrast agent (if both take place on the same day) |
| gastroscopy | • gastroscopy and irrigation not both during one day<br>• an ultrasound may not be made on the same day |

FIG. 6C

| Examination / Procedure | Rule |
|---|---|
| puncture | • all planned examinations before a puncture (five hours bed rest after a puncture) currently not realizable (intestinal biopsy, gastroscopy with biopsy, colonoscopy with biopsy, endoscopy, rectoscopy, are carried out in surgery, and are thus not available as information in the SAS) |
| stomach x-rays | • either before a gastroscopy with biopsy or one day afterwards |
| irrigation | • either before colonoscopy with biopsy or three days afterwards |
| MR-Cholangio | • either before endoscopy or two days afterwards |
| rectal sonography | • before a rectal sonography, no rectoscopy or colonoscopy. if this has already been done: wait one day |
| intestinal biopsy | • after an intestinal biopsy, no irrigation for 14 days |
| colonoscopy | • no colonoscopy before a abdominal puncture or drainage; if this has already been done: wait three days |
| ultrasound | • always before colonoscopy, or 1-3 days afterwards |

FIG. 7

| Field | Description |
|---|---|
| <Case> | Designation for the defined case (number of the case). |
| <Examination Code1> | The first examination code to be checked. Pages or nodes (in this case, the entry is valid for this node and for all pages under this node) can be inputted. If the entry remains empty, the rule for each found examination is applied. |
| <Examination Code2> | The second examination code to be checked. Pages or nodes (in this case, the entry is valid for this node and for all pages under this node) can be inputted. If the entry remains empty, the rule for each found examination is applied. |
| <Interval1> | The significance of this value depends on the defined case. If only one interval value is used, this value is always entered in the field <Interval1>. The field <Interval2> is used only if 2 interval values are used.<br><br>Format DD:HH:MM |
| <Interval2> | The significance of this value depends on the defined case<br><br>Format DD:HH:MM |

FIG. 8A

| Field | Description |
|---|---|
| <Info1> | This field prescribes the conditions that must be fulfilled for ExaminationCode 1 in order for the rule to be applied.<br><br>The items of information consist of groups of short descriptors of the RAL catalog, groups of operators and the associated value stores.<br><br>...<shortdescr1>;<hidden>;<Operator1>;<Value1.1>;<Value1.2>,...,<Value1.n>;<Operator2>;<Value2.1>,<Value2.2>,...,<Value2.n>,...,<Operatorn>;<Valuen.1>,<Valuen.2>,...,<Valuen.n><shortdescr2>;<hidden>;<Operator1>;<Value1.1>,...<br><br><table><tr><td><shortdescr></td><td>Is a short descriptor of the entry in the RAL catalog; it always begins with "/t"</td></tr><tr><td><hidden></td><td>This indicates whether the value is supposed to be displayed in the info dialog or not. If hidden=N, it is displayed; if hidden=Y it is not displayed but rather is read out from the database and cannot be modified. This entry must be the same for the same <shortdescr>.</td></tr><tr><td><Operator></td><td>operator that is applied to the value (possible entries: =,>,>=,<,<=,<>)</td></tr><tr><td><Value></td><td>element from the value store that must be selected in the info dialog in order for the rule to be applied</td></tr></table> |
| <Info2> | prescribes the conditions that must be fulfilled for examination code 2 in order for the rule to be applied; format as for Info1<br><br>...<shortdescr1>;<hidden>;<Operator1>;<Value1.1>;<Value1.2>,...,<Value1.n>;<Operator2>;<Value2.1>,<Value2.2>,...,<Value2.n>,...,<Operatorn>;<Valuen.1>,<Valuen.2>,...,<Valuen.n><shortdescr2>;<hidden>;<Operator1>;<Value1.1>,... |

FIG. 8B

| Case | Entry | Description |
|---|---|---|
| 1 | 1\US.USPAB\GI.IR R\3:00:00\\\ | An ultrasound puncture in the abdominal area is to be carried out before an irrigation. If the irrigation is already planned, the puncture should be planned at an interval of three days before the irrigation. |
| 1 | 1\CT.CTAB\MR\1:00 :00\\/t*;N;=;Barium\ | A CT abdominal examination using barium contrast agent is to be carried out before an MR examination. If the MR is already planned, the CT abdominal examination should be planned at an interval of one day before the MR examination.<br><br>In order to incorporate the dependency on age, for example the following entry is additionally required: |
| 1 | 1\CT.CTAB\MR\3:00 :00\\/t*;N;=;Barium*/t Age;Y;>;70\ | If the CT abdominal examination uses barium as a contrast agent, and the age (of the patient) is greater than 70 years, then if the MR is already planned the CT should have an interval of three days before the MR examination. |
| 1 | 1\\GI.IRR\6:00:00\\/t *;N;=;Barium\ | An examination using barium contrast agent is to be carried out before an irrigation. If the irrigation is already planned, the barium contrast agent examination should be planned at an interval of six days before the irrigation. |
| 1 | 1\US\GI.IRR\3:00:00 \2:00:00\\ | Three days before an ultrasound examination, and two days after an ultrasound examination, no irrigation may be planned. |
| 1 | 1\CT\MR\1:00:00\1: 00:00\\/t*;N;=;Yes,O ral,Barium\\/t*;N;=;Y es,Oral,Barium | A CT examination using contrast agent and an MR examination using contrast agent must be separated by an interval of one day. |
| 2 | 2\CT.CTPU\0:05:0 0\\\ | If there is a CT puncture among the planned examinations, it should be planned as the last examination (should receive the latest appointment time). If a CT puncture is already planned, all newly planned examinations should have an interval of at least five hours before this puncture. |

FIG. 9

| Field | Description |
|---|---|
| <shortdesc> | Short descriptor of the RAL catalog entry, without "/t" |
| <Heading> | Heading of the column in the info dialog described by a segment in the <Info> field |
| <SQL statement> | database field in which the items of information selected from a combo box in the info dialog are stored, OR, if the value is not to be displayed (hidden=Y), here there is an SQL statement that replaces the input in the info dialog. |
| <Connection condition> | Where-condition for storing of the database field |
| <Type> | Specifies the type of the value store: S for a string, N for a numerical value, B for a bitfield |
| <Type-dependent> | Dependent on the type of the value store: <table><tr><td>S</td><td>Inifile section in verdll.ini, in which the value store for the combo box of this column is in the value dialog.</td></tr><tr><td>N</td><td><Minimum value>\<Maximum value>. The value store is generated between these values (each natural number including these values).</td></tr><tr><td>B</td><td>Bit number that is queried.</td></tr></table> |

FIG. 10

| shortdesc | longdesc | Meaning |
|---|---|---|
| /tContrast | Contrast\Contrast agent\examination3.p17\examination2.fld_uid=examination3.fld_uid\\S\Contrast agent | Here the heading of the column in the info dialog is Contrast Agent, the items of information concerning the contrast agent already stored in an earlier examination processing are located in database field examination3.p17, the where-condition is examination2.fld_uid=examination3.fld_uid, and the value supply is a string list, and stands in the section Contrast Agent in the verdll.ini |
| /tAge | Age\Age\datediff(year,patient,birth_date,getdate()),0\(examination.fld_uid = examination2.fld_uid) and (examination.pat_ckey=patient.pat_ckey)\\N\0\120 | Here the age is determined via the formula datediff(year,patient,birth_date,getdate()), the where-condition is (examination.fld_uid = examination2.fld_uid), and (examination.pat_ckey = patient.pat_ckey), and the value supply is a numerical field that is generated between the minimum value 0 and the maximum value 120. |

FIG. 11

|  | Examination | Examination code |
|---|---|---|
| Cranial coil | Brain | MR_GEH |
|  | Rear cranial cavity | MR_HSG |
|  | Temporal lobe | ? |
|  | Sella | MR_SEL |
|  | Intracer. Angio | ? |
|  | Jaw capitulum | ? |
|  | Hand | MR_HD |
|  | Metatarsus | MR_FU |
|  | Orbita | MR_ORB |
|  | Paranasal sinuses | MR_NNH |
|  | Ear | MR_OHB |
| Cervical [neck] coil | Cervical vertebrae | MR_HWS |
|  | Neck or throat | MR_HA |
|  | Carotid angio | MR_AAC |
| Knee coil | Knee | MR_KN |
|  | Ankle joint | MR_SP |
|  | Lower leg | MR_USB |
| Body coil | Liver | MR_LEB |
|  | Pancreas | MR_PAN |
|  | Heart | MR_COR |
|  | Kidneys | MR_NIE |
|  | Kidney angio | ? |
|  | Upper leg | MR_OSB |
|  | Lower leg | MR_USB |
|  | Aorta | MR_AOT |
|  | ISG | MR_ISG |
|  | Coxa [hip] | MR_HU |
|  | Lower abdomen | MR_UB |
|  | Plexus brachialis | ? |
| Flex coil | Shoulder | MR_SC |
|  | Upper arm | MR_OAB |
|  | Elbow | MR_EL |
| Annular coil | Wrist | MR_HD |
|  | Sternoclavicular joint | MR_STG |
| Thoracic coil | Breast [or: chest] | MR_MAM |
| Spinal column coil | Cervical spinal column | MR_HWS |
|  | Thoracic spinal column | MR_BWS |
|  | Lumbar spinal column | MR_LWS |

FIG. 12

| Case | Exam 1 | Exam 2 | Int 1 | Int 2 | Contrast agent | Contrast agent during exam |
|---|---|---|---|---|---|---|
| 1 | Ultrasound | Gastroscopy | 1 | | | |
| 1 | US | GI | | | | |
| 1 | Abdominal puncture | Irrigation | 3 | | | |
| 1 | US.USPAB,CT.CTPAB | GI.IRR | | | | |
| 1 | Abdominal puncture | Gastroscopy | 3 | | | |
| 1 | US.USPAB,CT.CTPAB | GI | | | | |
| 1 | Drainage | Irrigation | 3 | | | |
| 1 | CT.DR,US.USDAB,MR.MRDR | GR.IRR | | | | |
| 1 | Drainage | Gastroscopy | 3 | | | |
| 1 | CT.DR,US.USDAB,MR.MRDR | GI | | | | |
| 1 | Abdominal ultrasound | ERCP | 1 | | | |
| 1 | US.USAB | GI.ERCP | | | | |
| 1 | MR | Biopsy | 7 | | | |
| 1 | MR | CT.CTPU,MR.MRPU,US.USPU | | | | |
| 1 | Ultrasound | Angiography | 24:00 | | | |

FIG. 13A

| Case | Exam 1 | Exam 2 | Int 1 | Int 2 | Contrast agent | Contrast agent during exam |
|---|---|---|---|---|---|---|
|  | US | ANG,INT,IVA |  |  |  |  |
| 1 | X-ray | Angiography | 24:00 |  |  |  |
| 1 | OP | ANG,INT,IVA |  |  |  |  |
| 1 | Angio | Irrigation | 3 |  |  |  |
| 1 | ANG,INT,IVA | GI.IRR |  |  |  |  |
| 1 | Angio | Stomach x-ray | 3 |  |  |  |
| 1 | ANG,INT,IVA | GI_MAG |  |  |  |  |
| 1 | Angio | Enteroclysma | 3 |  |  |  |
| 1 | ANG,INT,IVA | GI.ENT |  |  |  |  |
| 1 | Irrigation | Stomach X-ray | 3 |  |  |  |
| 1 | GI.IRR | GI.MAG |  |  |  |  |
| 2 | Spinal column or pelvic x-ray | Exam 2 | 1 | 7 | Oral | 2 |
| 2 | SK.WSB |  |  |  |  |  |
| 2 | Abdominal CT | MR | 1 | 2 | Barium | 1 |
| 2 | CT.CTAB | MR |  |  |  |  |

FIG. 13B

| Case | Exam 1 | Exam 2 | Int 1 | Int 2 | Contrast agent | Contrast agent during exam |
|---|---|---|---|---|---|---|
| 3 | Puncture | | 5:00 | | | |
| | CT.CTPU,MR.MRPU,US.USPU | | | | | |
| 4 | x-ray | Exam 2 | | | | 2 |
| | OP | | | | | |
| 41 | CT | Stomach x-ray | 7 | | Barium | 1 |
| 41 | CT | GI.MAG | 6 | | Barium | 1 |
| 41 | CT | Intestinal x-ray | 3 | | Barium | 1 |
| 41 | CT | GI.IRR | | | | |
| 41 | Exam 1 | Abdominal puncture | 3 | | Barium | 2 |
| | | US.USPAB,CT.CTPAB | | | | |
| 41 | Angiography | Exam 2 | 3 | | Barium | 2 |
| | ANG,INT,IVA | | | | | |
| 41 | IVU | Exam 2 | 7 | | Barium | 2 |
| | GU.IVU | | | | | |
| 42 | Bone density measurements | Exam 2 | | | Oral | 2 |

FIG. 13C

| Case | Exam 1 | Exam 2 | Int 1 | Int 2 | Contrast agent | Contrast agent during exam |
|---|---|---|---|---|---|---|
| 5 | SK.DEXA | | | | | |
| 5 | Rectal sonography | Irrigation | 3 | 2 | | |
| | US.REC | GI.IRR | | | | |
| 5 | Ultrasound | Irrigation | 3 | 2 | | |
| | US | GI.IRR | | | | |
| 6 | MR | | 1 | | | |
| | MR | | | | | |
| 6 | Gastroscopy | Irrigation | | | | |
| | GI | GI.IRR | | | | |
| 6 | Gastroscopy | Ultrasound | | | | |
| | GI | US | | | | |
| 6.1 | Angiography | CT | | | 2 | |
| | ANG,INT,IVA | CT | | | | |
| 6.1 | IVU | CT | | | 2 | |
| | GU.IVU | CT | | | | |
| 6.2 | MR | CT | | | | 1.2 |

FIG. 13D

SYSTEM AND METHOD FOR MEDICAL APPOINTMENT AND EXAMINATION SEQUENCE PLANNING

CROSS REFERENCE TO RELATED APPLICATIONS

This application claims the benefit of U.S. Provisional Application No. 60/507,658, filed Oct. 1, 2003. This provisional application is herein incorporated by reference.

BACKGROUND OF THE INVENTION

The invention relates to a system and method for optimizing medical appointment and examination sequence planning.

Many medical procedures involve numerous elements and/or steps that must be coordinated in a particular manner. Given the high costs for many of these procedures and the desire for minimizing the duration of such procedures (both for the convenience of the patient and to maximize efficiency of all parties and facilities related to them), it is desirable to optimize these procedures.

SUMMARY OF THE INVENTION

The present invention provides a system and method using auxiliary functions in order to provide automatic appointment planning of a sequence that is optimal, from a medical point of view, of the examinations and required minimum time intervals between examinations so that various factors, attributes and constraints can be taken into account in the appointment planning.

Moreover, these sequences and intervals can be utilized in manual appointment planning so that the user can be warned of an a problematic procedure. The system involves defining a set of rules and constraints and applying these rules and constraints to the sequencing of a series of medical examinations/procedures. The rules and constraints utilize a number of attributes, including, but not limited to: facility attributes, department attributes, equipment attributes, personnel attributes, patient attributes, and examination attributes. The set of rules and constraints can also incorporate an interaction of attributes. For example, a rule/constraint may consider both a patient attribute (e.g., weak, old) and an examination attribute (e.g., physically demanding) to limit the frequency of a particular examination (e.g., an x-ray) for a particular patient. Any combination of attributes may be incorporated into a particular rule/constraint.

The object of the invention is achieved by a computer-based automated method for creating or updating an optimized medical examination schedule comprising: creating an attributes database comprising sets of attributes, the sets of attributes comprising at least one of: facility attributes, department attributes, equipment attributes, personnel attributes, patient generic attributes, patient specific attributes, and medical procedure attributes; creating a rules table comprising rules records containing information or procedures obtained from one or more sets of attributes; inputting one or more medical examination procedures to be performed on a patient into a planned patient procedure list; for each examination in the planned patient procedure list, sequencing, by a sequencing module, the planned procedure list into an optimal examination schedule and providing time intervals between the procedures and checking, by a testing module, to ensure that the time intervals are possible to implement, utilizing the rules records from the rules table; and outputting either the error free optimal examination schedule or an error indication to a user.

The object of the invention is further achieved by a method for checking a medical examination schedule comprising: creating an attributes database comprising sets of attributes, the sets of attributes comprising at least one of: facility attributes, department attributes, equipment attributes, personnel attributes, patient generic attributes, patient specific attributes, and medical procedure attributes; creating a rules table comprising rules records containing information or procedures obtained from one or more sets of attributes; inputting one or more medical examination procedures to be performed on a patient into a planned patient procedure list; producing a proposed examination schedule based on the planned patient procedure list that includes time intervals between the exams; for each examination in the planned patient procedure list, checking, by a testing module, to ensure that the time intervals are possible to implement, utilizing the rules records from the rules table; and outputting an error message to the user when problems exist in the proposed examination schedule and outputting a success message when no problems exist in the proposed examination schedule.

The object of the invention is further achieved by a computer-based automated system for creating or updating an optimized medical examination schedule comprising: an attributes database comprising sets of attributes, the sets of attributes comprising at least one of: facility attributes, department attributes, equipment attributes, personnel attributes, patient generic attributes, patient specific attributes, and medical procedure attributes; a rules table comprising rules records containing information or procedures obtained from one or more sets of attributes; a planned patient procedure list containing procedures to be performed on a patient; a user interface configured for entering, by a user, into a computer of the system, attribute data for at least one of the sets of attributes and the planned patient procedure list; a sequencing and testing module configured to convert the planned procedure list into an optimal examination schedule containing procedures in sequence and respective optimized time intervals between procedures utilizing the rules records; and an output configured to display an optimal examination schedule or an error indication to the user.

An embodiment of this system is based on a project called MagicSAS, developed by Siemens AG and relates to an additional function that is used to determine examination sequences of the appointment/schedule planning module for the MagicSAS project. It is used both for adjusting the functionality of the system and implementing scheduling. It also provides a basis for testing, user documentation, and further development of the system.

An embodiment of the invention comprises a medical examination/procedure sequencing function that must first query a predetermined rule catalog and database (e.g., a control system) and search through the patient data for an occurrence of a particular sought examination(s). If this examination(s) is found, then this function determines an optimal sequence and defines a time interval between any two examinations. This optimal sequence and appertaining time intervals are also referred to as determined data.

If there is a new examination among the planned examinations, it is necessary to acquire additional information. For this purpose, in an embodiment of the invention, a dialog box of a user interface device is opened for the input or selection of this information, in which the desired value may be selected, e.g., via a combo box.

The following definitions are provided for the remainder of this document, unless otherwise specified. The interval "1 day" always means 24 hours. An examination is "deferrable" if it is in a current request and has not been authorized/certified. An examination is "authorized/certified" if it has a certified or an authorized status; an examination having this status can no longer be modified.

The following abbreviations are used throughout this document: contrast agent (KM), computer tomography (CT), magnetic resonance tomography (MR), renal X-ray (IVU), endoscopic retrograde colangio pancreatography (ERCP), Kaiser Franz Josef Hospital (KFJ).

DESCRIPTION OF THE DRAWINGS

The invention is described with respect to the preferred embodiments illustrated in the following drawings.

FIG. 4 is a computer screen shot illustrating an exemplary examination input dialog box;

FIG. 5 is a computer screen shot illustrating an exemplary interval warning/error message;

FIGS. 6A-C are parts of a table illustrating rules and constraints for various procedures in a particular case;

FIG. 7 is a table illustrating rules and constraints for various procedures in another case;

FIGS. 8A, B are portions of a table illustrating an exemplary record structure for and Exam Order catalog;

FIG. 9 is a table illustrating an exemplary table structure for an Exam Order catalog;

FIG. 10 is a table illustrating an exemplary record structure for an RAL catalog;

FIG. 11 is a table illustrating an exemplary table structure for an RAL catalog;

FIG. 12 is a table illustrating an exemplary equipment/component requirement list for various examinations; and FIGS. 13A-D are portions of a table illustrating various examination codes and intervals.

DETAILED DESCRIPTION OF THE PREFERRED EMBODIMENTS

Figure 1:
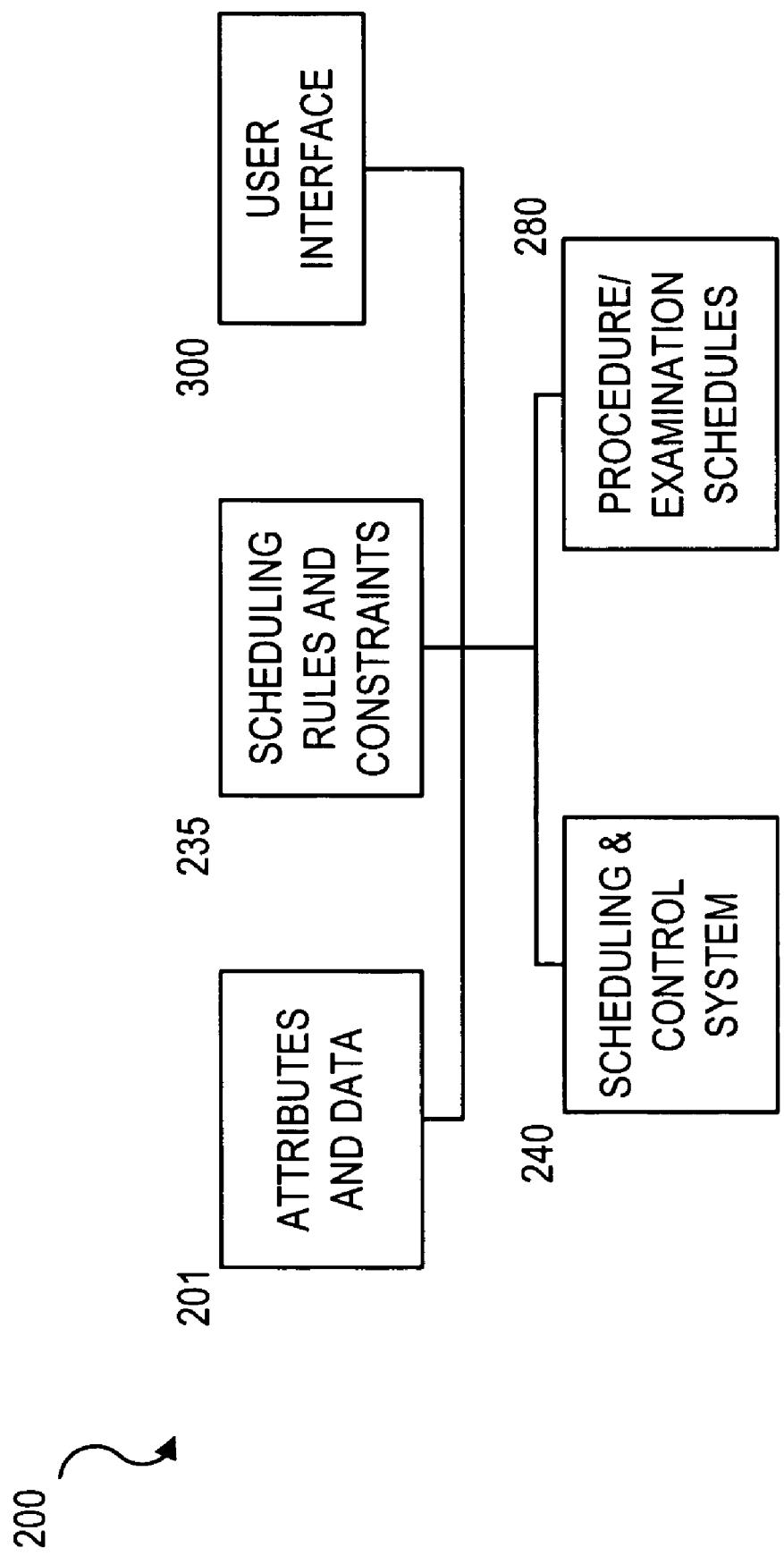
FIG. 1 is a block diagram illustrating the high-level system components.

FIG. 1 illustrates the high level system components that are utilized according to an embodiment of the invention. The inventive system 200 comprises a user interface 300 by which information is entered by and output to a user. The system utilizes procedure/examination schedules 305 that are utilized and modified by a scheduling and control system 240 utilizing both attributes and data 201 relevant for the scheduling in conjunction with scheduling rules and constraints 235 of the system.

Figure 2:
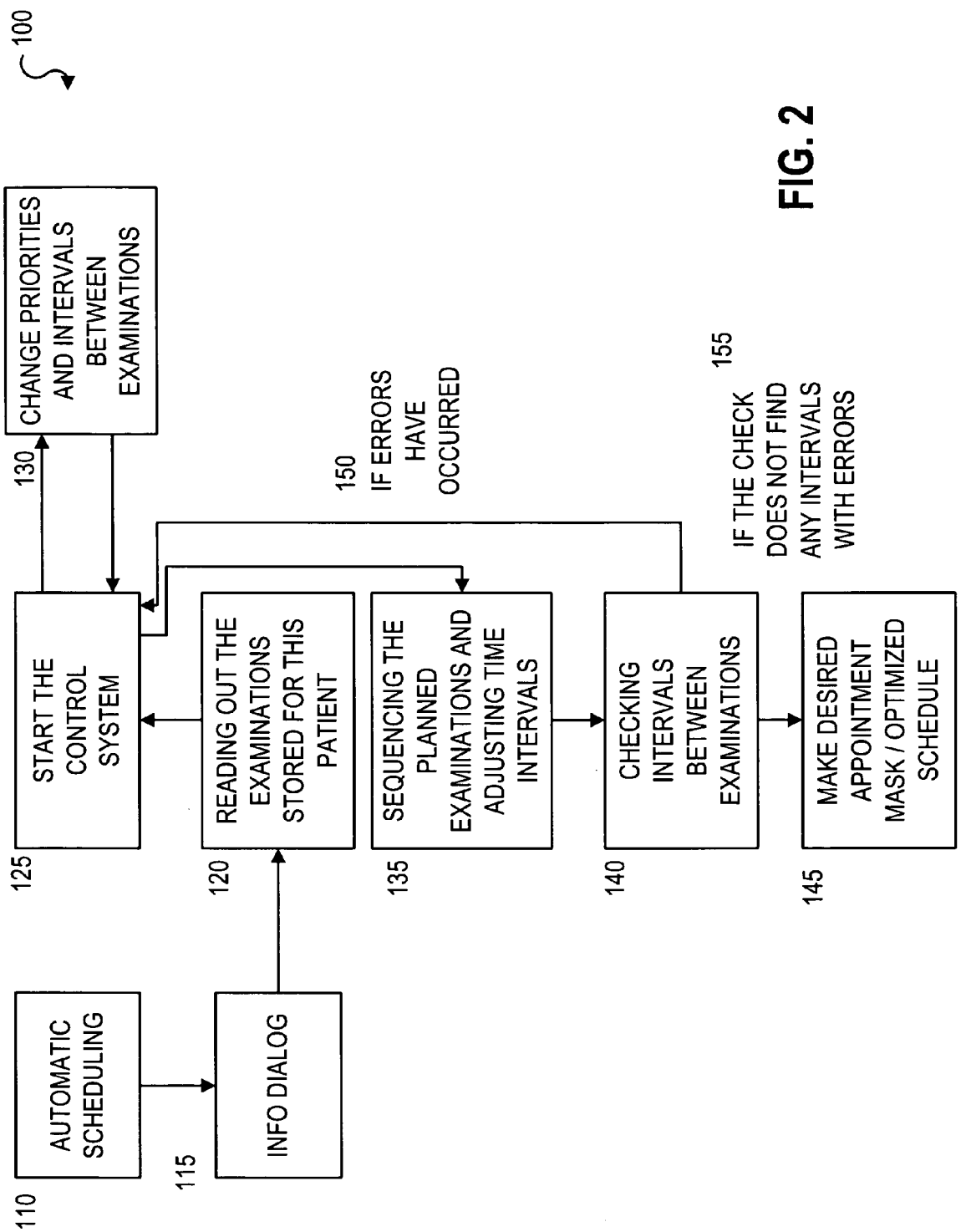
FIG. 2 is a flow diagram illustrating the overall medical examination scheduling procedure.
Figure 3:
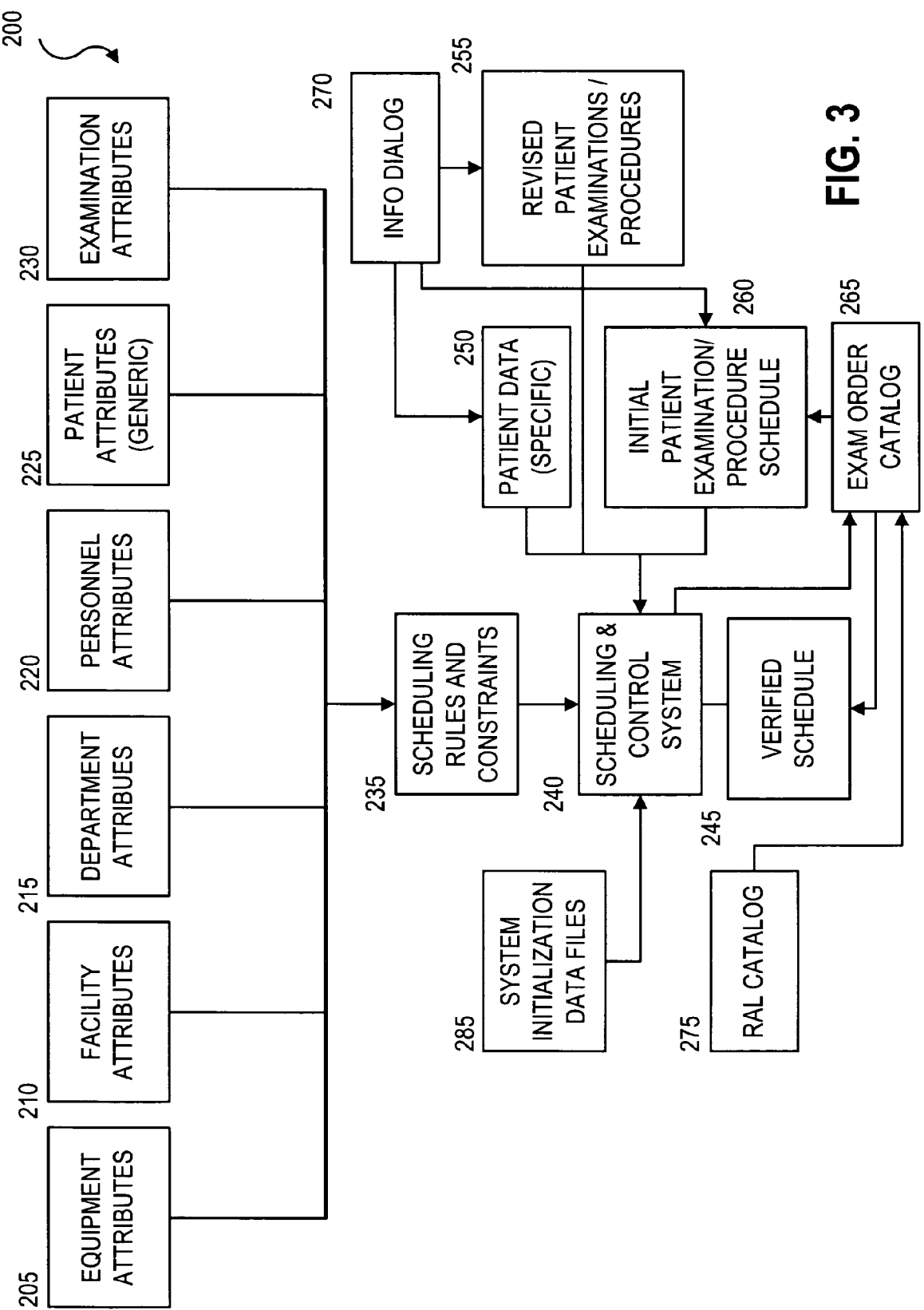
FIG. 3 is a block diagram illustrating the database and functional components related to the scheduling procedure.

FIG. 2 illustrates an overall view of an embodiment of the invention that illustrates the steps of producing a medical examination sequence as a procedure diagram 100. FIG. 3 illustrates the system components and data stores used to implement the planning function.

According to FIG. 2, a user may chose to perform automatic scheduling 110 for patient medical procedures. This presents the user with a mechanism to acquire information from the user, which may be in the form of an information gathering dialog box 115. The examinations that are stored for a particular patient are read out 120, and the control system that governs the scheduling of the procedures 125 is started. Additional examination information entered via the information dialog 115 can then be integrated with any other preexisting examination data that may exist within the system, and any changes in the priorities and intervals between the examinations is performed 130. The changes are then passed from the control system 125 to a routine that sequences the planned examinations and adjusts the time intervals 135. A check is then performed 140 to ensure that the intervals between the examinations are possible to implement. If errors have occurred 150, then the control system 125 process the schedule and changes to the priorities and intervals between examinations 130 are again implemented. If there are no problems with the schedule or intervals between examinations, then the appointment mask/examination schedule 145 is produced.

The scheduling functions of an embodiment of the present invention are embedded in the existing functionality of an overall medical support system as follows. The construction of the examination sequence for planned examinations is determined by initiating a sequence according in, e.g., one or more of the following ways:

upon selection of an "automatic scheduling" point in "planning" menu bar of an appointment planning module; or upon selection of an "automatic scheduling" button in a button bar of the appointment planning module; or given appointment planning of unscheduled services; or given a takeover of CIS (Clinical Information System: an information system for patient data) patients in a patient module; or upon actuation of an "automatic scheduling" button in a planning mask of a service module.

Afterwards, determined data (an ordering of the appointments and time intervals) is forwarded to a "desired appointment" mask.

The scheduling and testing may occur by generating a set of possible or incomplete schedules based on some subset of constraints and then utilizing the rules to eliminate or modify various schedules from this set as each respectively applicable rule, attribute, or other data would require modification.

Although the scheduling function is designed to operate in an automated scheduling context, it is still possible to utilize various subfunctions of the system with manual planning of an examination sequence. In the case of manual planning, system rules are also monitored, and if the time intervals or the sequence do not agree, a warning is generated (no further action has to occur in the manual scheduling operation).

In an embodiment of the invention, an initialization file may be utilized to determine if the scheduling function is activated or not (if, e.g., the product is licensed). Such an initialization file entry might be:

Sienet.ini [Scheduling plan] ExaminationOrder=ON

This "working" function may take into account only the data previously ascertained, and only already-stored examinations; i.e., if two users simultaneously plan, for one patient, for the examinations to which a rule applies, then this particular rule is not executed.

Figure 4:
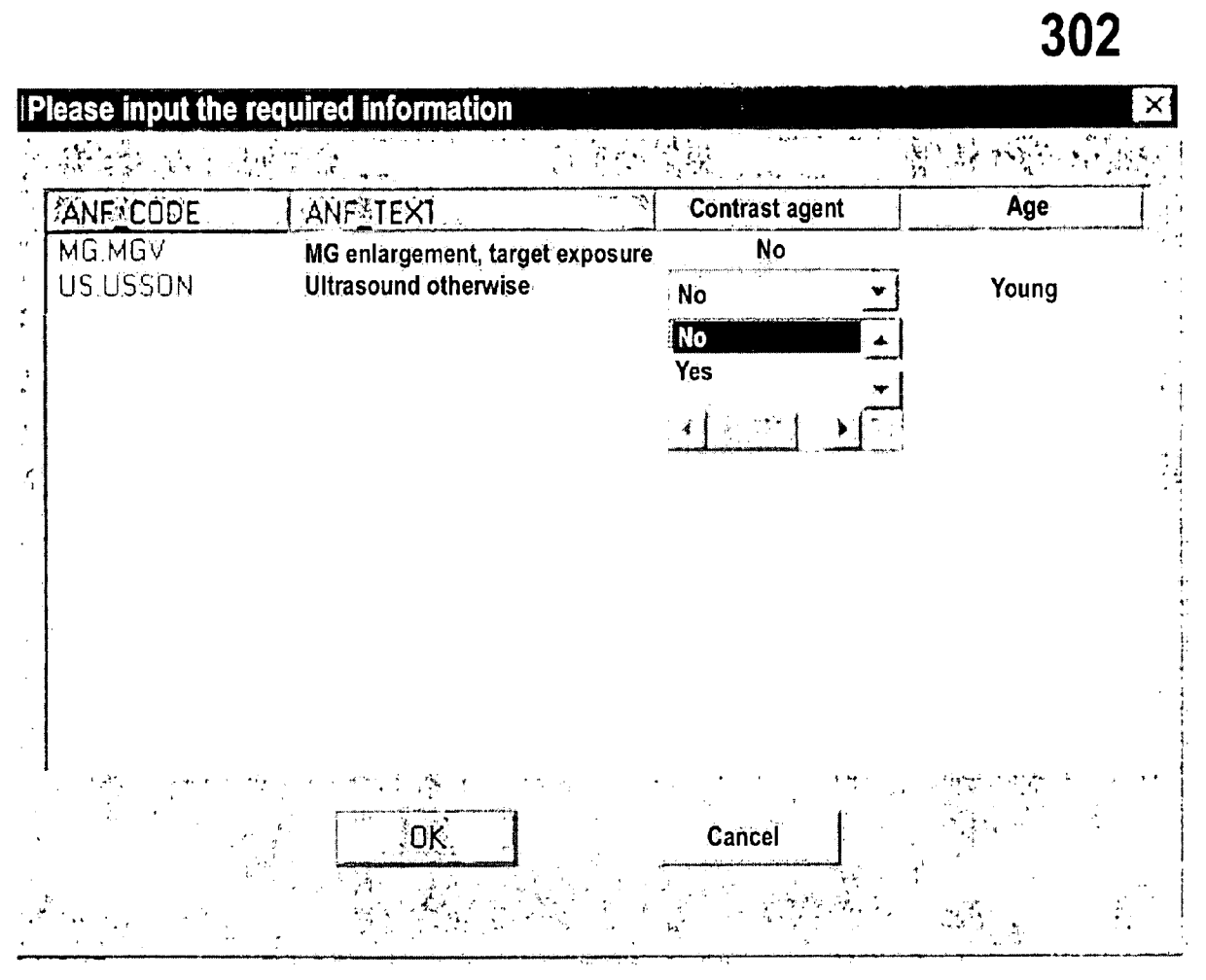

As illustrated in FIG. 3, when automatic scheduling is initiated according to one of the mechanisms described above, the system checks whether a new sub-examination is present among the sub-examinations that has not yet been stored (that does not have a data entry indicating the sub-examination has been processed, such as a UID folder) 255. If this is the case, an entry screen opens (e.g., a dialog box 200, FIG. 4) opens in which the required information for each examination can be input. FIG. 4 illustrates an exemplary input dialog box 200 with which the user can interact with the system and for specifying appointment/examination scheduling information.

The type of examination dictates what information is displayed and can be entered by the user. For the examination, the dialog 200 may comprise a variable number of columns, the corresponding field being deactivated for examinations for which a particular piece of information is not required. The precise configuration results from the entries in tables that are used to store examination information, such as an EXAM_ORDER Catalog 265 and RAL Catalog 275, described in more detail below.

In the input dialog box 200, the user can click on a field that displays possible options that contain an available store of values for a field. These stores of values can be read out from an initialization file 285 or generated automatically between two numerical values (minimum and maximum), and can thus be set freely. Items of information already stored can be overridden or modified.

When the user clicks indicates that all information has been entered, e.g., by clicking an OK button in the input dialog box 200, the entered information is stored and the control system 240 is started. The system now reads the catalog information that has been entered by the user, e.g., in the info dialog 270, reads all examinations planned for the patient in a particular time frame 255, and also takes over the already-planned requests 260.

Each case and record described in the catalog (e.g., the EXAM_ORDER Catalog 265) is queried. If one of the examinations listed there is found in the already-planned requests 260 or is among the examinations planned in a particular time period for this patient, then decisions are made differently according to the particular case: if both examinations are in the already-planned requests and have no scheduled appointment, then the sequence that is optimal according to the catalog is determined, and/or particular least intervals are set, and are handed over to the desired-appointment mask. If only one of the two examinations can be deferred, then, according to the rule, an interval is set to this examination (only if this results in further pushing back of the previous beginning time).

The optimal sequence of examinations, as well as the required intervals, are now displayed. These sequences and intervals can also be modified by the user, but this will disturb the optimal sequence.

After the automated planning function executes (and after manual appointment planning as well), a testing function is activated that indicates where one of the rules defined in the control system has been infringed and that displays the required interval, as well as offering the possibility of correcting this error. See FIG. 5 for an exemplary dialog box display 300 of an interval warning for a given examination.

By way of example, an embodiment of the invention is illustrated with two cases that illustrate the application of influencing factors. For partial examinations that are newly planned, after the planning date, the starting time and intervals can be set. For already-stored examinations, only later times, never earlier ones, can result. The following data for the examination sequence can be installed in a control system which is then implemented.

Examination Sequence for Case 1

FIG. 6A-C illustrates exemplary rule/constraint data for Case 1 for the examination system that may be installed in the scheduling and control system 240.

Control System Psuedo-Code for Case 1

For the psuedo-code listings of the control system 240 below, words in boldface stand for equipment groups, words in italics stand for examination codes, and underlined words designate the interval between examinations. "Default" means that here the value is used that is standardly set in, e.g., an equipment group catalog. The "find" function is designed to check the data of the selected patient and look for the sought examination. For this purpose, the request code of the examination is provided to this function; the function checks whether there has been such an examination and takes the one closest to the current date. It stores the date of this examination, and its status (whether it is deferrable).

The ordering function takes as parameters the found examinations and the proposed interval, checks whether the examinations can be deferred, and puts them in the list of equipment groups of a "desired appointment" mask, at the corresponding point. Moreover, the interval between the examinations is set to the required value. The ordering function can also modify the beginning of the search.

For Case 1, Examination 1 takes place either at a time interval A2 before Examination 2 or a time interval A1 after Examination 2. Both examinations can have additional parameters that are monitored (e.g., contrast agent).

```
If find(Examination1) AND find(Examination2) &&
Condition(Examination1) == TRUE &&
Condition(Examination2) == TRUE
{
   If (Examination2 == deferrable)
   {
      if (Examination1 == deferrable)
      {
         Ordering(Examination1, A2, Examination2)
      }
   }
   else
   {
      if (BeginDate Exam2 < BeginDate Exam1 - Interval 1)
      {
         //Here nothing should happen, because Examination2
            can remain as it is
      }
      else
      {
         Ordering(Examination1, A2, Examination2)
      }
   }
   else if (Examination1 == deferrable)
   {
      if(BeginDate Exam1 < BeginDate Exam2-Interval2)
      {
      //Here as well nothing should happen, because Exam1 can
         remain as it currently is
      }
      else
      {
         Ordering(Examination2, A1, Examination1)
      }
}
```

Case 1 Pseudo-Code

Control System Psuedo-Code for Case 2

FIG. 7 illustrates exemplary rule/constraint data for Case 2 for the examination system that may be installed in the scheduling and control system 240.

Control System Psuedo-Code for Case 2

In the Case 2 scenario, all planned examinations take place before Examination 1, or at the earliest time after the interval A1.

```
If find (Examination1)
{
   If Examination1 == deferrable
   Then Ordering(Examination1 (max))
   Else
   {
      if(BeginDate Exam2 < BeginDate Exam1 – Interval2)
      {
      }
      else
      {
         Ordering(Examination1,A1,Examination2)
      }
   }
}
```

In this way, through prioritization, Examination 1 is pushed to the end of the appointment list, that is, all currently planned examinations are to take place before Examination 1.

Recursion

The following illustrates recursion in the use of planning. In the planned examinations, the problem can occur that the finally valid beginning time points are not yet fixedly determined. In some circumstances, this can result in the setting of false intervals. An example of this is illustrated as follows. A GI.IRR has been planned for 1 May 2003, and stored. Then, on May 2, a CT and an MR are additionally planned. Here, e.g. 2 rules apply: (1) CT and MR 3 days after GI; (2) MR 1 day after CT. There are now the following possibilities for the execution of the rules (for each examination there is the end of the previous examination to which the rule applies (or at the beginning of the planning date) and the interval to this examination).

TABLE 1

|    | at begin | 3 days | 3 days, 1 day | 1 day | 1 day, 3 days | 1 day, 3 days, 1 day |
|----|----------|--------|---------------|-------|---------------|----------------------|
| GI | 1.5., 0  |        |               |       |               |                      |
| CT | 2.5., 0  | 1.5., 3| 1.5., 3       | 2.5., 0|1.5., 3       | 1.5., 3              |
| MR | 2.5., 0  | 1.5., 3| 4.5., 1       | 2.5., 1|1.5., 3       | 4.5., 1              |

It can be seen that different "begin time points" result for CT and MR, according to which rule is executed first. However, if, after the first pass through, the rules are applied again, the correct result is obtained.

For this reason, after the first pass, the monitoring function is started that checks the set appointments (end of the previous examination+set interval), and, if an interval having an error is been determined, the monitoring function executes the control system again. This takes place a maximum of the number of times that a rule was executed in the first pass (thus, twice in the above example), i.e., recursively. If it is not possible to obtain an error-free result within these passes, a warning is output.

Examination Codes & EXAM_ORDER Catalog

Referring to FIG. 3, the information pertaining to the examination/procedure sequencing may be stored in an entity called an EXAM_ORDER Catalog 265. This catalog stores examination sequencing information for a particular patient and is modified by the scheduling module and control system 240.

Since different examination codes exist in every hospital for one and the same examination, the examination code should be input at the beginning for a particular examination/procedure for a patient. The EXAM_ORDER Catalog 265 includes examination codes for the individual cases.

In a preferred embodiment, the EXAM_ORDER Catalog 265 comprises multiple records, one for each examination, that is structured into fields as illustrated in FIG. 8A, B. The format of the long descriptor of the EXAM_ORDER catalog runs as follows:

<Case>\<ExaminationCode1>\<ExaminationCode2>\<Interval1>\<Interval2>\<Info1>\<Info2>

An example for an Info1 entry might be:
/Contrast agent;N;=;Yes,Oral,Barium*/Age;Y;>;20, (nothing indicated for Info2)

This means that for Examination Code 1, the items of information "Contrast agent" can be entered in the info dialog 270, while the items of information for the age, due to the value Y(es) for Hidden, are not displayed, but are calculated. If Yes, Oral or Barium have been entered there for "Contrast agent" and the calculated age (which is determined from the database using the formula found in the corresponding RAL entry) is more than 20 years, the condition is fulfilled and the rule is applied. The individual operators are likewise AND-connected; that is, all operators having associated possibilities should be satisfied for the condition to be fulfilled.

FIG. 9 illustrates the structure of an exemplary EXAM_ORDER Catalog 265 for a patient.

RAL Catalog

An embodiment of the invention may utilize an RAL Catalog 275 to provide information regarding medical examinations. FIG. 10 illustrates an exemplary record structure that may be utilized for the RAL Catalog 275. The RAL Catalog 275 should contain entries corresponding to the items of information in the EXAM_ORDER Catalog 265; i.e., the shortdesc that was defined in an information field of the EXAM_ORDER Catalog 265 must also be defined in the RAL Catalog. 275. The name of the short descriptor always begins with "/t".

The long descriptor may comprise:

<shortdesc>\<Heading>\<SQL statement>\<Connection condition>\\<Type>\<Type-dependent>

An exemplary RAL Catalog 275 is illustrated in FIG. 11.

For the exemplary RAL Catalog 275, bitfields must always be hidden, because they are not modified (here it is checked only whether particular bits are set or not). If a bitfield is given as a type, then it should be indicated in the ExamOrder Catalog 265 which bits are to be set. For this purpose, the numerical value that results when the desired bits are set are input.

For example: if one wishes to check whether bits 1, 2, 6 and 7 have been set, then as a value in the ExamOrder catalog, 1(1.Bit)+2(2.Bit)+32(6.Bit)+64(7.Bit)=99 would be entered.

The scheduling and control system 240 utilizes data from the following sources. Data is provided for all examinations for the planned patients, from which the required ones are then sought. Default intervals are then obtained for each respective examination. The date and the status of the found examination and the examination codes and prescribed intervals retrieved from the EXAM_ORDER Catalog 265.

System initialization data files 285 may be used to hold system-wide information required by the scheduling and control system 240. Examples of these initialization data files in an embodiment of the invention are illustrated in the following table.

TABLE 2

Exemplary Initialization File Settings

| Exemplary Init. File | Value/Setting |
|---|---|
| Sienet.ini | In the section "appointment plan", the switch "Examination Order" should be set to ON. |
| termsrvdll.ini | A section "timespan" should be present in which the entries SearchPast and SearchFuture have to be supplied with values. These indicate how far in the past or future the database is to search for already-existing examinations (default: SearchPast = 30; SearchFuture = 365). |
| verdll.ini | a section (Name = name of the section indicated in entries in the RAL catalog of <type> "S") should be present in which the respective entries (numbers beginning with 0) should be supplied with values. These are the value supplies for the combo boxes that appear in the info dialog. |

Error Handling

If, after the determination of the optimal sequence, the interval is modified to a value below the required minimum value, or the sequence is altered, a warning is displayed that shows the two examinations, the set interval, and the required interval (FIG. 5). According to the exemplary user display illustrated in FIG. 5, clicking on "Ignore" results in the appointments being normally stored, while a click on "Correct" takes the user back to the planning mask. Here, the items of information input after the manual planning during the storing can also be modified.

In the event that particular rules/constraints have not been entered into the system (e.g., a particular holiday, work hours, or unknown examination type), it is possible that even in the first search (or in later ones), an appointment may be found that breaks a rule.

For example: a user plans for today, Friday, at 20:00, a CT abdominal examination using a barium contrast agent; on Monday a GI.IRR is planned for 08:00. The rule says: Abdominal CT with barium contrast agent either before an irrigation or six days thereafter. The system sets as a starting time Friday at 20:00, and no interval. The search algorithm now seeks an appointment time, but does not find one until Monday after the irrigation (no work hours are defined for Sat. and Sun.). However, this appointment time violates a rule.

In this situation, the system produces an interval warning message during the storing of the appointment. If two examinations are planned using the same equipment group to which a rule applies, this schedule cannot be carried out without problems because the appointment times are sought only for equipment groups, not for partial examinations.

Exemplary Rules/Constraints

The following information was determined based on research and interviews with medical personnel performed at the Kaiser-Franz-Josef Hospital, but is easily generalizable to other medical settings. This information relates to normal, routine operation, and not to acute or life-threatening situations.

General Information

Various constraints on the system involve general resources that are available to a medical facility. Equipment, layout, and arrangement constraints should be considered by the scheduling system. For example, at the KFJ Hospital, in the X-ray center, with the tomography center and mammography center, there are seventeen examination devices in six areas. Overlapping of equipment may be a factor as well, since it is possible for an apparatus to be assigned to two areas, but only one area can use it at a time (e.g., ultrasound apparatus for the ultrasound and mammography departments). Scheduling constraints must also be considered. There are often special days on which only particular examinations are carried out (and possibly at particular times).

Constraints pertaining to personnel must also be considered. For example, there may be more medical apparatuses available than there are trained technicians to use them; for this reason, the examinations should be planned so that a technical assistant is available to run a particular apparatus. Or a particular facility may only have a physician and technical assistant available on Monday, from 08:00 until 09:15, and, for example, on Wednesday from 08:00 to 09:00 there may be times at which other events are occurring, e.g., voluntary continuing education sessions, during which time no appointments may be scheduled in many areas.

Further constraints involve transportation of patients to examinations. For example, at one facility, each pavilion group has an automobile in which two lying and three seated patients, or six seated patients, can fit; thus, for example one cannot plan to take three lying patients from a pavilion group at the same time. However, it is quite probable that as many patients of a station will be given appointments at the same time as can be transported in an automobile.

All of these general constraints ideally should be included in the scheduling system.

In addition to organization level constraints, there are department-level constraints that must further be included in the scheduling system. The following department-level constraints exemplify the types of constraints that could be included for a particular facility.

CT Department

CT Department General Considerations

In a CT department, the following medical constraints could be integrated into the scheduling system:

CT using contrast agent containing barium before a stomach/intestinal examination or three to six days thereafter.

Angiography and CT with barium contrast agent not to be carried out on the same day.

IVU and CT with contrast agent are not to be done on the same day, if they are to be carried out separately. If they are to be combined (with administering of contrast agent), first the CT and then the IVU is carried out.

Endosonography before CT with oral contrast agent, or one day afterward.

One cannot perform an MR with contrast agent and a CT with contrast agent on the same day; at least one day must elapse.

For interventions, punctures, and drainages, the patient must have an empty stomach; for this reason, an appointment is set for the morning.

CT Department Organizational/Facility Specific Considerations

There may be additional constraints imposed by a particular facility related to a specific department. For example, there may be equipment and/or technical constraints that are integrated into the scheduling system. These might include specific functionalities of specific machines. At one exemplary facility in the CT department, e.g., biopsies can be carried out at an Apparatus 2, but these might be of longer duration (approximately 1 hour), whereas an osteo-CT (bone density measurements) might be performed only on an Apparatus 1.

The following illustrates a series of exemplary constraints that may be provided with respect to a CT department from the standpoint of a particular facility:

In the context of a follow-up exam, outpatients standardly receive a morning appointment. In-patients are given an appointment on the same day.

No reserve appointments are left open.

There are fixed appointments for certain stations; for example: radiation therapy Mondays, Wednesdays and Thursdays at 08:00 and 12:00; neurology daily at 15:00.

Certain examinations are made on particular days; for example, osteo-CT exams are always on Saturdays.

From a personnel standpoint, the following exemplary constraints could be considered for the CT department of a particular facility:

Examinations in which the immediate presence of a physician is not required are made for 07:00 (exams not using contrast agent, e.g., paranasal sinuses, ears).

Routine operation runs from 07:00 to 19:00; the last CT appointment should be made for 18:30.

Biopsies are carried out only in the morning.

No appointments are made during continuing education periods.

Radiology Department

Radiology Department General Considerations

Various general considerations could be considered for a radiology department. The following medical constraints are exemplary of such general considerations:

First, the x-rays are made (abdominal, renal, skeletal, pelvic, lumbar spinal column), then a contrast agent exam is carried out where applicable.

For bone x-rays (in the abdominal region, e.g., lumbar, pelvic), no contrast agent exams using contrast agent containing barium are to be made beforehand.

Bone x-rays of the spinal column or of the pelvis are to be made either before a contrast agent exam using contrast agent containing barium or 3-6 days later.

For lumbar bone density measurements, an oral contrast agent is in no case to be used; after a week, normal results are again obtained.

After a puncture, no x-ray may be made in which the patient is moved a great deal (e.g., stomach/intestinal x-ray). After a thoracic puncture, however, a lung check-up x-ray must be made.

The age of the patient is taken into account. Children and older patients cannot remain on an empty stomach for long, and are thus given precedence.

Diabetics should also obtain as early an appointment as possible, and should be examined quickly (if they must be examined on an empty stomach).

IVU either before an exam using a barium contrast agent or 3-6 days afterward.

Radiology Department Organizational/Facility Specific Considerations

The following illustrates a series of exemplary constraints that may be provided with respect to a radiology department from the standpoint of a particular facility:

There are 4 X-ray apparatuses; one is used only for standing lung x-rays; the other can be used for all types of exams (2 for standing, 3 for lying).

Lying patients are standardly examined in Room A, mobile ones in Room B; renal x-rays are made in Room C.

Currently, there are no upper limits for x-ray examinations per patient (but this can be prescribed by the physician).

Per apparatus, 1-2 times per day a reserve appointment of 30 minutes is entered (for emergency cases), but these may not remain open in the appointment planning module, because it is otherwise booked full; Thus, an empty appointment might be entered. If this appointment is not required, it must be booked at the proper time.

A routine operation goes from 08:00 to 13:00, but can be expanded by the physicians on duty.

Skeletal and lung x-rays are not scheduled.

Appointments are assigned within one week.

In case of tardiness, the patient is either taken anyway or is given a new appointment.

On Saturdays, only acute patients are seen (no regular appointments).

MR Department

MR Department General Considerations

Various general considerations could be considered for an MR department. The following medical constraints are exemplary of such general considerations:

For different exams, the coils for the exam must be changed; for this reason similar exams are done in succession There are no safe interactions with CT contrast agent containing iodine.

In an MR cholangio (upper abdominal) exam, the patient must have an empty stomach; thus s/he is given a morning appointment.

MR cholangio either before endoscopy or 2 days afterward.

Routinely, no more than one MR in one day, or more than two in a week (more is unusual).

If after an abdominal CT (contrast agent containing barium) it is desired to perform an MR exam in the same region, the contrast agent has a disturbing effect; for this reason a wait of at least 1 day is made, or at least 2 days if the patient is 70 or older.

Exemplary Equipment Requirements

The system may further incorporate an identification of a specific type of equipment or equipment component required for a particular type of examination. The exemplary table illustrated in FIG. 12 relates to an MR coil type used for a particular examination. Although this table relates to MR examinations, such a table is easily extendible for other types of examinations.

MR Department Organizational/Facility Specific Considerations

The following illustrates a series of exemplary constraints that may be provided with respect to a radiology department from the standpoint of a particular facility:

The assistants' routine work begins at 07:30; first knee examinations are done (no contrast agent, immediate presence of a physician not required).

Mammography Department

Mammography Department General Considerations

Various general considerations could be considered for a mammography department. The following medical constraints are exemplary of such general considerations:

After a biopsy, an MR can be made after a week at the earliest.

Time duration of the examinations: mammography and ultrasound: 30 minutes; mammotomography: 60 minutes; ultrasound biopsy: 30 minutes; mammotomography+ultrasound biopsy: 90 minutes.

The state of the patient influences the duration of the examination (this is seldom known beforehand).

Mammography Department Organizational/Facility Specific Considerations

The following illustrates a series of exemplary constraints that may be provided with respect to a mammography department from the standpoint of a particular facility:

- A mammography is always followed by an ultrasound, but only the mammography is entered in the appointment planning (30 minutes are reserved). However, there are differing opinions and services offered.
- The physicians' hours end at 13:00, so mammotomography biopsies should be scheduled for 11:00 (beginning time) at the latest, ultrasound biopsies for 11:30, and mammographies for 12:00 (beginning time) at the latest.
- In case of uncertainty as to whether an ultrasound or a mammotomography biopsy should be done (the physician decides), a mammotomography biopsy appointment is entered. (The apparatus has to be calibrated—the preliminary work is then already done).
- Outpatient appointments are scheduled for within one week, in-patient ones within 1-2 work days, unless the patient desires otherwise. In assigning outpatient routine mammographies, the patient's menstrual cycle is taken into account (first to tenth day).
- No time held in reserve—"normally" no unregistered patients are seen.
- Saturday appointments are made only in exceptional cases.
- Because there are only two assistants and one authorizing physician, a maximum of two exams can be performed simultaneously.
- For one physician, the following fixed exams can be planned per day:
- 4 interventions (biopsies and marking) and 6 mammographies (with ultrasound)
- In the case of fewer interventions, more mammographies can be done (up to 10 if there are 0 interventions=20 exams).

Ultrasound Department

Ultrasound Department General Considerations

Various general considerations could be considered for an ultrasound department. The following medical constraints are exemplary of such general considerations:

- After administering of a barium contrast agent (irrigation, passage through small intestine, stomach x-ray), there should be a wait of 2-3 days before performing an ultrasound.
- Diabetics and children are seen as early as possible.
- In the case of MRSA patients and those having other infectious diseases (e.g., HIV), due to the risk of infection, these patients are seen only at the end, but must be registered beforehand.
- All planned examinations before a puncture (five hours bed rest after a puncture).
- Before a rectal sonography, no irrigation, rectoscopy, or colonoscopy. If already performed: after irrigation, wait 2-3 days, after rectoscopy and colonoscopy wait one day.
- After a colonic polypectomy, no irrigation for 14 days.
- Endosonography before CT using oral contrast agent, or one day thereafter.
- Abdominal sonography before ERCP (Endoscopic Retrograde Colangio Pancreatography).

Ultrasound Department Organizational/Facility Specific Considerations

The following illustrates a series of exemplary constraints that may be provided with respect to an ultrasound department from the standpoint of a particular facility:

- Abdominal examinations are scheduled for the morning (on both apparatuses) due to the requirement of an empty stomach. Afterwards, Apparatus 1 is used predominantly for abdominal examinations, and Apparatus 2 is used predominantly for examinations of "small parts" (throat, joints, lymph nodes).
- The examination is not a burden on the patient; therefore there are no limits on examinations per day.
- The average duration of the examinations is 15 minutes, except for punctures (up to 60 minutes) and vascular Doppler ultrasound (30 minutes).
- Patients are scheduled either from 08:15 to 11:30 or for 12:30 (with reserve "gaps").
- On Mondays and Wednesdays, appointments are assigned starting from 09:15 (due to continuing education sessions for physicians and assistants).
- Appointments within one week for inpatients, or 2-3 weeks for outpatients (if not urgent).
- Each Thursday, approximately 10 patients come from the oncological ambulance; two one-hour "gaps" are left open between 09:00 and 11:00.
- Only acute cases are seen on Saturdays.

2nd Medical Station General Considerations:

Various general considerations could be considered for a radiology department. The following medical constraints are exemplary of such general considerations:

- Irrigation requires two days preparation, ultrasound one day.
- Gastroscopy and irrigation are not to be performed on the same day.
- After a colonoscopy (large intestine imaging) or gastroscopy, no ultrasound can be done on the same day.
- No irrigation for four days after an intestinal biopsy.

Angiography Department

Angiography Department General Considerations

Various general considerations could be considered for an angiography department. The following medical constraints are exemplary of such general considerations for angiography: vascular examinations:

- Exam duration (diagnostic): 45-90 minutes.
- Interventional angiography: two hours 30 minutes to four hours.
- Before an angiography: no irrigation, stomach examinations, enteroclysma or examinations using barium contrast agent (wait three days).
- A physician is required for each examination.
- Only one angio/day per patient, because angiography is a very invasive examination and due to the quantity of contrast agent administered.
- The daily course of examinations in the angiography area begins with interventions (difficult), followed by diagnostic examinations.
- Diabetics are not given preferential treatment (patients may take a small breakfast and drink plenty of liquid), except for examinations under general anesthetic.
- Physicians' qualifications must be taken into account during planning; i.e., physicians in training still may not conduct certain examinations alone.

Angiography Department Organizational/Facility Specific Considerations

The following illustrates a series of exemplary constraints that may be provided with respect to an angiography department from the standpoint of a particular facility:

- There is only one room; a second can be used except on Wednesday and Thursday, together with an x-ray examination.

Maximum number of examinations per day per room: 5-6 diagnostic pelvis/leg examinations or one larger intervention and one selective angiography and 2-3 pelvis/leg examinations or three interventions.

Diagnostic examinations mostly acute (performed on the day of scheduling or on the next day), interventions must be scheduled (general anesthetic may be necessary; specific materials not present).

X-Ray Department

X-Ray Department General Considerations

Various general considerations could be considered for an x-ray department. The following medical constraints are exemplary of such general considerations:

First irrigation, then stomach (1-2 days).

Ultrasound either before an x-ray examination or three days thereafter (due to administering of contrast agent)

X-Ray Department Organizational/Facility Specific Considerations

The following illustrates a series of exemplary constraints that may be provided with respect to an x-ray department from the standpoint of a particular facility:

Two rooms (with x-ray apparatuses).

An average of eight patients per room (only one room is fixed, the other is shared with angio).

In-patients are scheduled according to the type of examination; acute patients are seen immediately.

7.3 Examination Codes and Intervals:

FIG. 13A-D is a table illustrating various exemplary examinations with examination codes, intervals, and additional data related to the examinations. The cases used in this table are the same Case 1 and Case 2 described above. For the intervals, whole numbers designate calendar days; numbers having a decimal point designate a number of hours.

For the purposes of promoting an understanding of the principles of the invention, reference has been made to the preferred embodiments illustrated in the drawings, and specific language has been used to describe these embodiments. However, no limitation of the scope of the invention is intended by this specific language, and the invention should be construed to encompass all embodiments that would normally occur to one of ordinary skill in the art.

The present invention may be described in terms of functional block components and various processing steps. Such functional blocks may be realized by any number of hardware and/or software components configured to perform the specified functions. For example, the present invention may employ various integrated circuit components, e.g., memory elements, processing elements, logic elements, look-up tables, and the like, which may carry out a variety of functions under the control of one or more microprocessors or other control devices. Similarly, where the elements of the present invention are implemented using software programming or software elements the invention may be implemented with any programming or scripting language such as C, C++, Java, assembler, or the like, with the various algorithms being implemented with any combination of data structures, objects, processes, routines or other programming elements. Furthermore, the present invention could employ any number of conventional techniques for electronics configuration, signal processing and/or control, data processing and the like.

The particular implementations shown and described herein are illustrative examples of the invention and are not intended to otherwise limit the scope of the invention in any way. For the sake of brevity, conventional electronics, control systems, software development and other functional aspects of the systems (and components of the individual operating components of the systems) may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device. Moreover, no item or component is essential to the practice of the invention unless the element is specifically described as "essential" or "critical". Numerous modifications and adaptations will be readily apparent to those skilled in this art without departing from the spirit and scope of the present invention.

What is claimed is:

1. A computerized, automated method for scheduling medical facility procedures that medically treat or examine respective patients, said medical facility procedures being available in a medical facility that interacts with said patients, said medical facility being comprised of a plurality of facility departments and having a plurality of different types of medical equipment respectively for implementing different ones of said medical facility procedures, said method comprising the steps of:

creating an electronic database by entering data through an input unit into an electronic storage unit that represent sets of attributes that influence each of said medical facility procedures that are available at said medical facility, said data comprising a set of facility attributes that describe said medical facility, a set of department attributes that describe the respective facility departments, a set of equipment attributes that describe said medical equipment, a set of personnel attributes that describe personnel at said medical facility who operate said medical equipment at said medical facility, a set of patient generic attributes that describe common characteristics of said patients who interact with said medical facility, a set of patient-specific attributes describing a specific patient to be scheduled for interaction with said medical facility, and a set of facility procedures attributes that describe the respective medical facility procedures that are available at said medical facility;

in a processor having access to said electronic database in said electronic storage unit, automatically creating an electronic rules table that is independent of date and time availability of said medical facility procedures at said medical facility, from at least two of said sets of attributes, that impose requirements and constraints for implementing said medical facility procedures at said medical facility on said specific patient, said requirements and constraints defining at least one of an order in which at least two of said medical facility procedures must take place relative to each other, and a time duration that must exist between any two of said medical facility procedures;

entering, into said processor, an electronic description of a plurality of prescribed medical procedures, selected from among said medical facility procedures, to be performed on said specific patient at said medical facility and, in said processor, formulating a planned patient procedure list comprising said plurality of prescribed medical procedures for said specific patient;

in an electronic sequencing module supplied with said planned procedure list by said processor, automatically conducting a calendar date and time of day search for data and time availability for each of the prescribed medical procedures in said planned procedure list and organizing the prescribed medical procedures in said planned patient procedure list into an initial optimized schedule comprising a date and time sequence for the prescribed medical procedures in the planned patient procedure list;

in a testing module communicating with said sequencing module, automatically checking whether said initial optimized schedule conforms to said rules table by determining whether said initial optimized schedule satisfies all requirements and avoids all constraints imposed by said rules table;

when said initial optimized schedule is determined by said testing module to conform to said rules table, making said initial optimized n schedule available as a humanly perceptible output from said sequencing module as a final examination schedule to be implemented; and when said initial optimized schedule does not conform to said rules table, automatically, in said electronic sequencing module, conducting a further calendar date and time of day search for date and time availability of each of the prescribed medical procedures in said planned procedure list and organizing the prescribed medical procedures in said planned patient procedure list into a revised optimized schedule comprising a revised date and time sequence for the prescribed medical procedures in the planned patient procedure list until a revised optimized schedule is organized that, as determined by said testing module, conforms to the rules table, and emitting the revised optimized schedule that conforms to the rules table as a humanly perceptible output from said sequencing module as a final examination schedule to be implemented, and if no revised optimized schedule can be found that conforms to said rules table, emitting a humanly perceptible error indication from said testing module.

2. The method according to claim 1, further comprising:
in said processor, automatically determining if all needed information is present for each of the procedures in the planned patient procedure list or sets of attributes; and
if it is not emitting a humanly perceptible output from the processor, prompting the user to input the additional information needed.

3. The method according to 1, further comprising:
adding or removing a patient procedure by the user to the planned patient procedures list after the optimal examination schedule has been sequenced; and
in said processor, sequencing a modified optimal examination schedule that is based on the newly added or newly removed patient procedure.

4. The method according to claim 1, further comprising:
modifying data within the sets of attributes or rules records; and
in said processor, sequencing a modified optimal examination schedule that includes the modified attribute or rule data.

5. The method according to claim 1, further comprising:
initiating the sequencing by a user command in an appointment planning or service module.

6. The method according to claim 1, further comprising:
initiating the sequencing by a separate computer-based process or system.

7. The method according to claim 1, further comprising:
in said processor, providing a sequencing function activation switch in an initialization file to indicate if the sequencing function is activated or not.

8. The method according to claim 1, further comprising:
manually modifying, by the user, the optimal examination schedule.

9. The method according to claim 1, further comprising:
from said processor providing possible corrective actions to the user when a sequencing error is encountered; and
allowing selection, by the user, one of the provided possible corrective actions.

10. The method according to claim 1, further comprising:
from said processor providing an indication as to whether one or more of the procedures are deferrable; and
in said processor, automatically modifying the sequenced optimal examination schedule when one or more of the procedures are indicated as being deferrable.

11. The method according to claim 1, further comprising:
in said processor, recursively executing the sequencing and checking to produce the optimal examination schedule.

12. The method according to claim 1, further comprising:
in said processor, organizing the rules table by associating rules records with a respective patient procedure.

13. The method according to claim 1, further comprising:
from said processor, obtaining information for the sequencing and testing with an SQL query into the attributes database.

14. A method as claimed in claim 1 comprising at said input unit, displaying a dialog box for entering said sets of attributes.

15. The method according to claim 2, further comprising:
displaying options for the user to select from when inputting the additional information needed.

16. The method according to claim 4, further comprising:
automatically initiating the sequencing by the modifying f the attribute or rules data.

17. The method according to claim 6, wherein the separate computer-based process or system is a clinical information system for patients.

18. The method according to claim 14, further comprising:
displaying, within the dialog box, a variable number of columns, one or more of which contains a deactivated field when additional data is not required.

19. The method according to claim 14, further comprising:
automatically initiating the sequencing in said processor by the adding a patient procedure to or removing a patient procedure from the plurality of procedures in said planned patent procedure list.

20. A computerized, automated system for scheduling medical facility procedures that medically treat or examine respective patients, said medical facility procedures being available in a medical facility that interacts with said patients, said medical facility being comprised of a plurality of facility departments and having a plurality of different types of medical equipment respectively for implementing different ones of said medical facility procedures, said system comprising:
an electronic storage unit and an input unit connected thereto allowing entry of data through the input unit into the electronic storage unit that represent sets of attributes that influence each of said medical facility procedures that are available at said medical facility, said data comprising a set of facility attributes that describe said medical facility, a set of department attributes that describe the respective facility departments, a set of equipment attributes that describe said medical equipment, a set of personnel attributes that describe personnel at said medical facility who operate said medical equipment at said medical facility, a set of patient generic attributes that describe common characteristics of said patients who interact with said medical facility, a set of patient-specific attributes describing a specific patient to be scheduled for interaction with said medical facility, and a set of facility procedures attributes that describe the respective medical facility procedures that are available at said medical facility;

processor having access to said electronic storage unit configured to automatically create an electronic rules table that is independent of date and time availability of said medical facility procedures at said medical facility, from at least two of said sets of attributes, that impose requirements and constraints for implementing said medical facility procedures at said medical facility on said specific patient, said requirements and constraints defining at least one of an order in which at least two of said medical facility procedures must take place relative to each other, and a time duration that must exist between any two of said medical facility procedures;

said processor having an input allowing entry into said processor of an electronic description of a plurality of prescribed medical procedures, selected from among said medical facility procedures, to be performed on said specific patient at said medical facility, and said processor being configured to formulate a planned patient procedure list comprising said plurality of prescribed medical procedures for said specific patient;

an electronic sequencing module supplied with said planned procedure list by said processor configured to automatically conduct a calendar date and time of day search for data and time availability for each of the prescribed medical procedures in said planned procedure list and to organize the prescribed medical procedures in said planned patient procedure list into an initial optimized schedule comprising a date and time sequence for the prescribed medical procedures in the planned patient procedure list;

a testing module communicating with said sequencing module, configured to automatically check whether said initial optimized schedule conforms to said rules table by determining whether said initial optimized schedule satisfies all requirements and avoids all constraints imposed by said rules table;

said testing module being configured, when said initial optimized schedule is determined by said testing module to conform to said rules table, to make said initial optimized schedule available as a humanly perceptible output from said sequencing module as a final schedule to be implemented; and said electronic sequencing module being configured, when said initial optimized schedule does not conform to said rules table, to automatically conduct a further calendar date and time of day search for date and time availability of each of the prescribed medical procedures in said planned procedure list and to organize the prescribed medical procedures in said planned patient procedure list into a revised optimized schedule comprising a revised date and time sequence for the prescribed medical procedures in the planned patient procedure list until a revised optimized schedule is organized that, as determined by said testing module, conforms to the rules table, and to emit the revised optimized schedule that conforms to the rules table as a humanly perceptible output from said sequencing module as a final examination schedule to be implemented, and said testing module being configured, if no revised optimized schedule can be found that conforms to said rules table, to emit a humanly perceptible error indication from said testing module.

\* \* \* \* \*